(12) United States Patent
Huynh et al.

(10) Patent No.: US 11,938,337 B1
(45) Date of Patent: Mar. 26, 2024

(54) LIGHT AND VIBRATION THERAPY DEVICE AND METHOD THEREFOR

(71) Applicant: LEBOW, LLC, Bothell, WA (US)

(72) Inventors: Sang Phu Huynh, Ho Chi Minh (VN); Thai Quan Nguyen, Ben Tre (VN); Nga Thi Thanh Nguyen, Bothell, WA (US); Tuong Huu Tran, Can Tho (VN); Dang Minh Lu, Ben Tre (VN); Phuoc Thi Le Tran, Ho Chi Minh (VN)

(73) Assignee: Nga Nguyen, Holly Springs, NC (US)

( * ) Notice: Subject to any disclaimer, the term of this patent is extended or adjusted under 35 U.S.C. 154(b) by 1017 days.

(21) Appl. No.: 16/730,891

(22) Filed: Dec. 30, 2019

(51) Int. Cl.
*A61N 5/06* (2006.01)
*A61H 23/02* (2006.01)
*A61M 21/00* (2006.01)

(52) U.S. Cl.
CPC ....... *A61N 5/0618* (2013.01); *A61H 23/0254* (2013.01); *A61H 2023/0272* (2013.01); *A61H 2201/0146* (2013.01); *A61H 2201/5012* (2013.01); *A61H 2201/5046* (2013.01); *A61H 2201/5058* (2013.01); *A61M 2021/0044* (2013.01); *A61N 2005/0652* (2013.01)

(58) Field of Classification Search
CPC ...... A61N 5/06; A61N 5/0613; A61N 5/0618; A61N 5/0622; A61N 2005/0643; A61N 2005/065; A61N 2005/0651; A61N 2005/0652; A61H 23/00; A61H 23/02; A61H 23/0245; A61H 23/0254; A61H 2023/0272; A61H 2201/0142; A61H 2201/0146; A61H 2201/0149; A61H 2201/5007; A61H 2201/501; A61H 2201/5012; A61H 2201/5046; A61H 2201/5058; A61H 2201/5061; A61H 2201/5064

USPC ....... 607/88, 108–111; 601/2, 15, 18, 19, 24
See application file for complete search history.

(56) References Cited

U.S. PATENT DOCUMENTS

| | | | |
|---|---|---|---|
| 2014/0128780 A1* | 5/2014 | Kennedy | A61B 17/12118 604/20 |
| 2018/0228681 A1* | 8/2018 | Iverson | A61H 1/00 |
| 2018/0369064 A1* | 12/2018 | Baxter | A61F 7/02 |
| 2019/0357771 A1* | 11/2019 | Yu | A61N 5/0613 |
| 2021/0093887 A1* | 4/2021 | Dijkstra | A61N 5/0616 |
| 2022/0134049 A1* | 5/2022 | Sakuma | A61H 1/001 600/28 |

FOREIGN PATENT DOCUMENTS

JP 2019-030196 * 2/2019 ............. A61H 23/02

* cited by examiner

*Primary Examiner* — Ahmed M Farah
(74) *Attorney, Agent, or Firm* — Larsen IP, PLLC

(57) ABSTRACT

A system and method for mind-body relaxation may include a plurality of vibration modules, a light-providing member, a controller, a relaxation substrate, a pillow member, a graphical user interface (GUI), and network connection circuitry.

58 Claims, 8 Drawing Sheets

LIGHT AND VIBRATION THERAPY DEVICE AND METHOD THEREFOR

SUMMARY

According to an embodiment, a system for mind-body relaxation includes a plurality of vibration modules, a light-providing member, and a controller. Each vibration module of the plurality of vibration modules is configured to provide a vibration to a respective predetermined body site of a user. The light-providing member is configured to provide light at a plurality of light positions viewable from a user relaxation position. The controller is operably connected to the plurality of vibration modules and the light-providing member, and is configured to control at least one of a light characteristic of the light provided by the light-providing member and a vibration characteristic of the vibration provided by each vibration module.

According to an embodiment, a method for inducing relaxation includes aligning a plurality of vibration units respectively to correspond to predetermined therapy sites of a user's body, positioning a plurality of light-providing areas within view of a user relaxation position, setting (e.g., via a controller) at least one vibration parameter of at least one vibration unit of the plurality of vibration units, setting (e.g., via the controller) at least one light parameter of a light-providing member. The controller receives an input to begin a therapy session. A vibration mode of each vibration unit of the plurality of vibration units may be selectively engaged consistent with the setting of the at least one vibration parameter. Light is selectively provided to the light-providing areas via the light-providing member consistent with the at least one light parameter.

DETAILED DESCRIPTION

Figure 1:
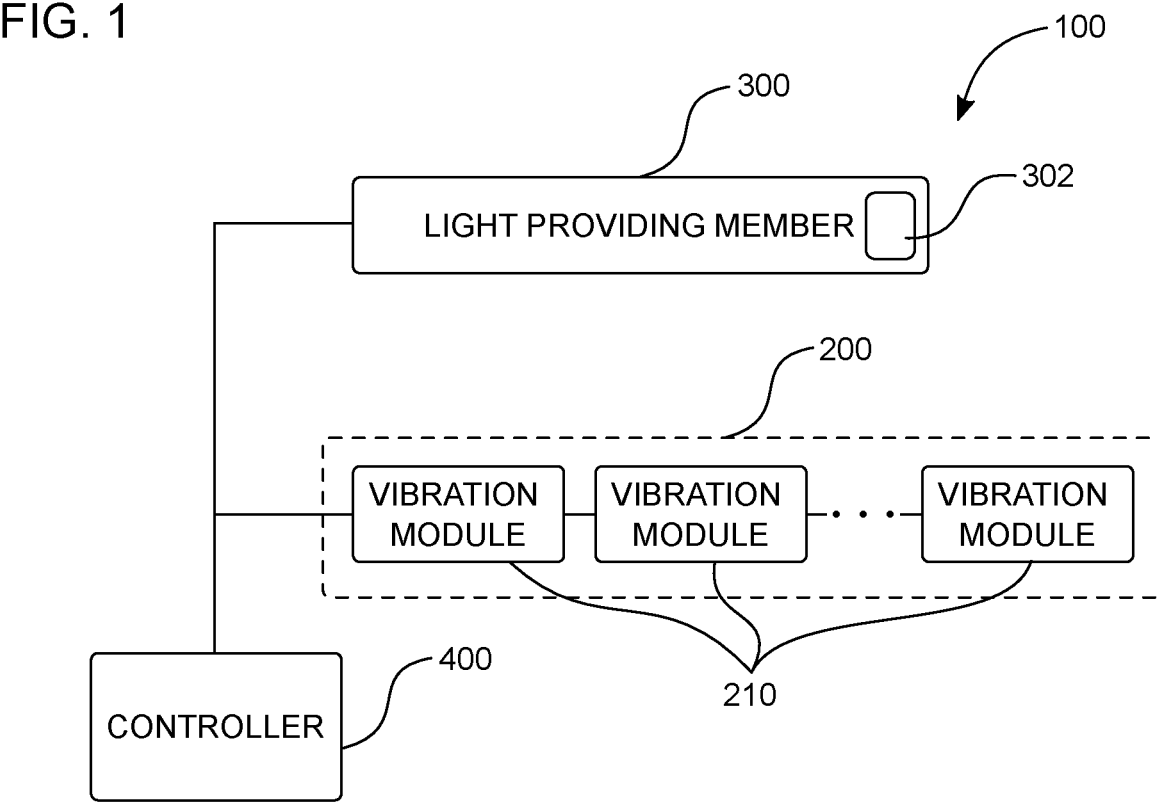
FIG. 1 is a block diagram of a system for mind-body relaxation, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

The applicants have recognized that conventional medicine does not provide a reliable means for treating stress, pain, and other maladies without side effects. For example, many pharmaceutical treatments, while affecting certain symptoms, often fail to treat the underlying cause of those symptoms. In many cases, disease and pain are related to—or at least exacerbated by—stress and pain. The applicants have thus recognized advantages from directing a user's mind in a way that permits the user's body to reduce, eliminate, or ignore, at least temporarily, the affects of stress and pain by reducing the root stress or pain. Specifically, the applicants have through experiments obtained a system to aid one in directing a user's mind with the aid of vibration and light provided in key therapeutic body areas, in key sequences.

In an example, a user may focus her mind on each of a series of lights, provided in a particular sequence synchronized with vibrations applied to nerve nodes at particular areas of the body. The lights may be provided in a prescribed sequence using particular colors, intensities, and other features to achieve a relaxation state. In one non-limiting example, a user may apply light and vibration to each of nine areas in a sequence moving from one therapeutic area to the next, each vibrating for 3 seconds, then off for 3 seconds. Alternatively, the time for on and off may be 1 second, 5 seconds, 9 seconds, 15 seconds, 30 seconds or 60 seconds. In one embodiment, the sequence may repeat for a present time, such as 5 minutes, 15 minutes, 30 minutes, 45 minutes, 1 hour, 3 hours, 5 hours, or 8 hours.

FIG. 1 is a block diagram of a system 100 for mind-body relaxation, according to an embodiment.

According to an embodiment, the system 100 includes a plurality of vibration modules 200, each vibration module 210 of the plurality of vibration modules 200 configured to provide a vibration to a respective predetermined body site of a user. The system 100 includes a light-providing member 300 configured to provide light at a plurality of light positions viewable from a user relaxation position, and a controller 400 operably connected to the plurality of vibration modules 200 and the light-providing member 300, the controller 400 configured to control at least one of a light characteristic of the light provided by the light-providing member 300 and a vibration characteristic of the vibration provided by said each vibration module 210.

Figure 2A:
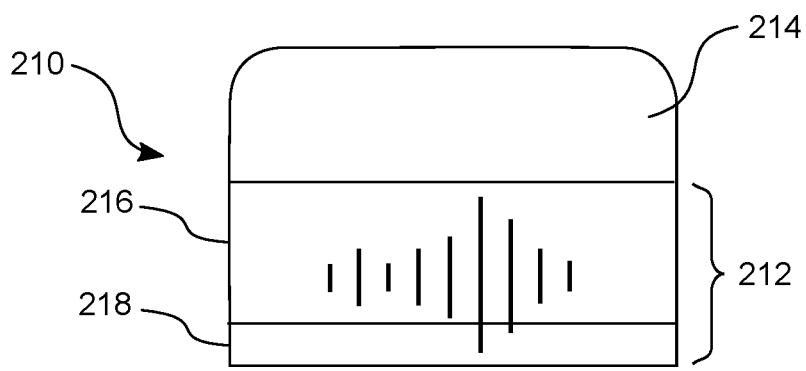
FIG. 2A is an illustration of a vibration module described in FIG. 1, according to an embodiment.

FIG. 2A is an illustration of the vibration modules 210 described in FIG. 1, according to an embodiment. In an embodiment, each vibration module 210 of the plurality of vibration modules 200 includes a vibration member 212. Each vibration member 212 may include a linear resonant actuator 216, and the controller 400 may include a current generator configured to energize the linear resonant actuator 216 with an oscillating current to cause linear oscillation of a mass of the linear resonant actuator 216. In another embodiment, each vibration member 212 includes an eccentric rotating mass vibration motor 216, and the controller 400 includes a current generator configured to energize the eccentric rotating mass vibration motor 216. Additionally and/or alternatively, each vibration module 210 further includes a cushion member 214. The cushion member 214 may be replaceable and may be selected from a plurality of cushion members respectively having at least one of a different thickness and a different firmness. In one embodiment, the vibration member 212 is disposed within the replaceable cushion member 214.

Figure 3:
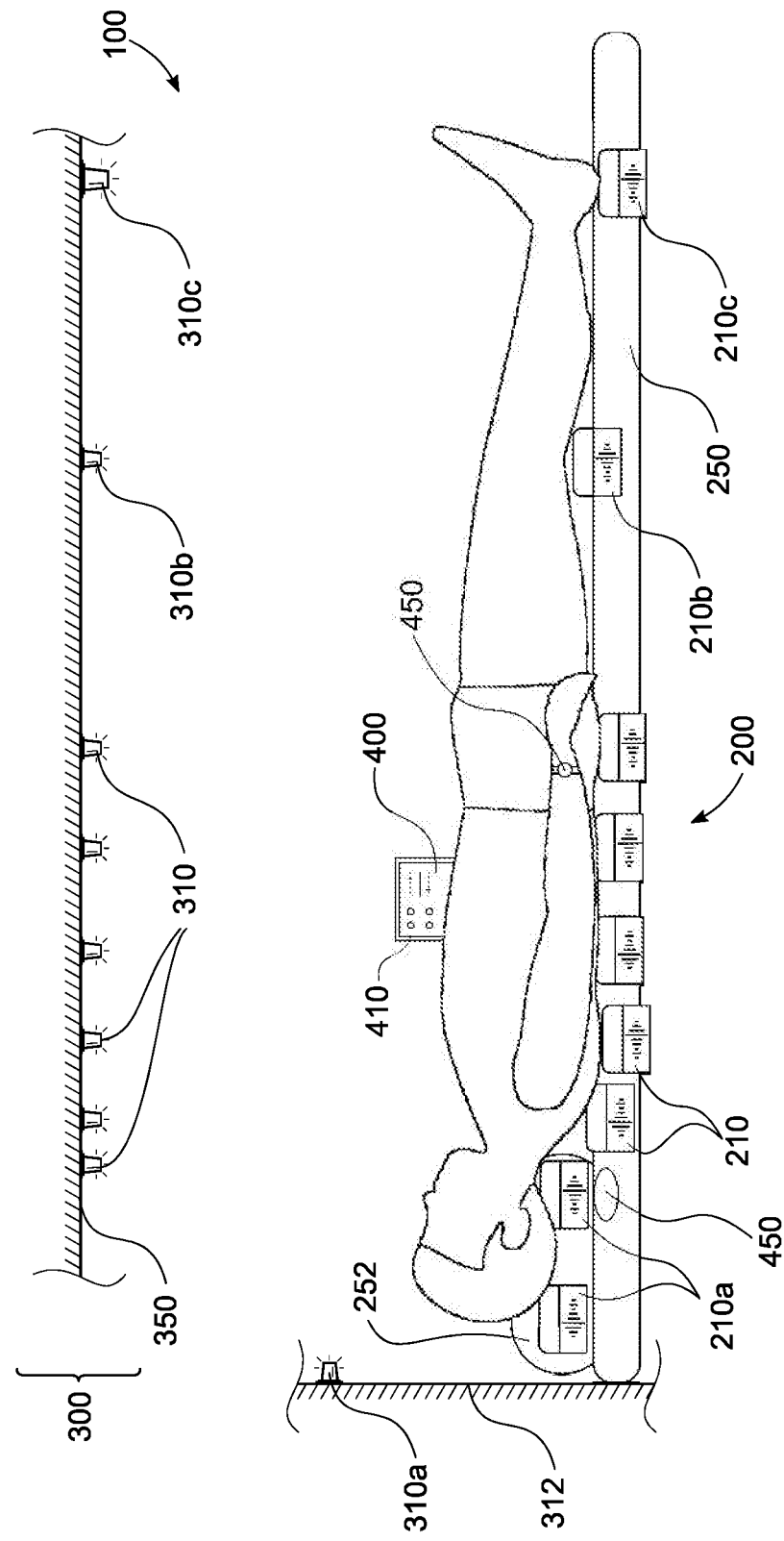
FIG. 3 is a detailed illustration of the system of FIG. 1, according to an embodiment.
Figure 4:
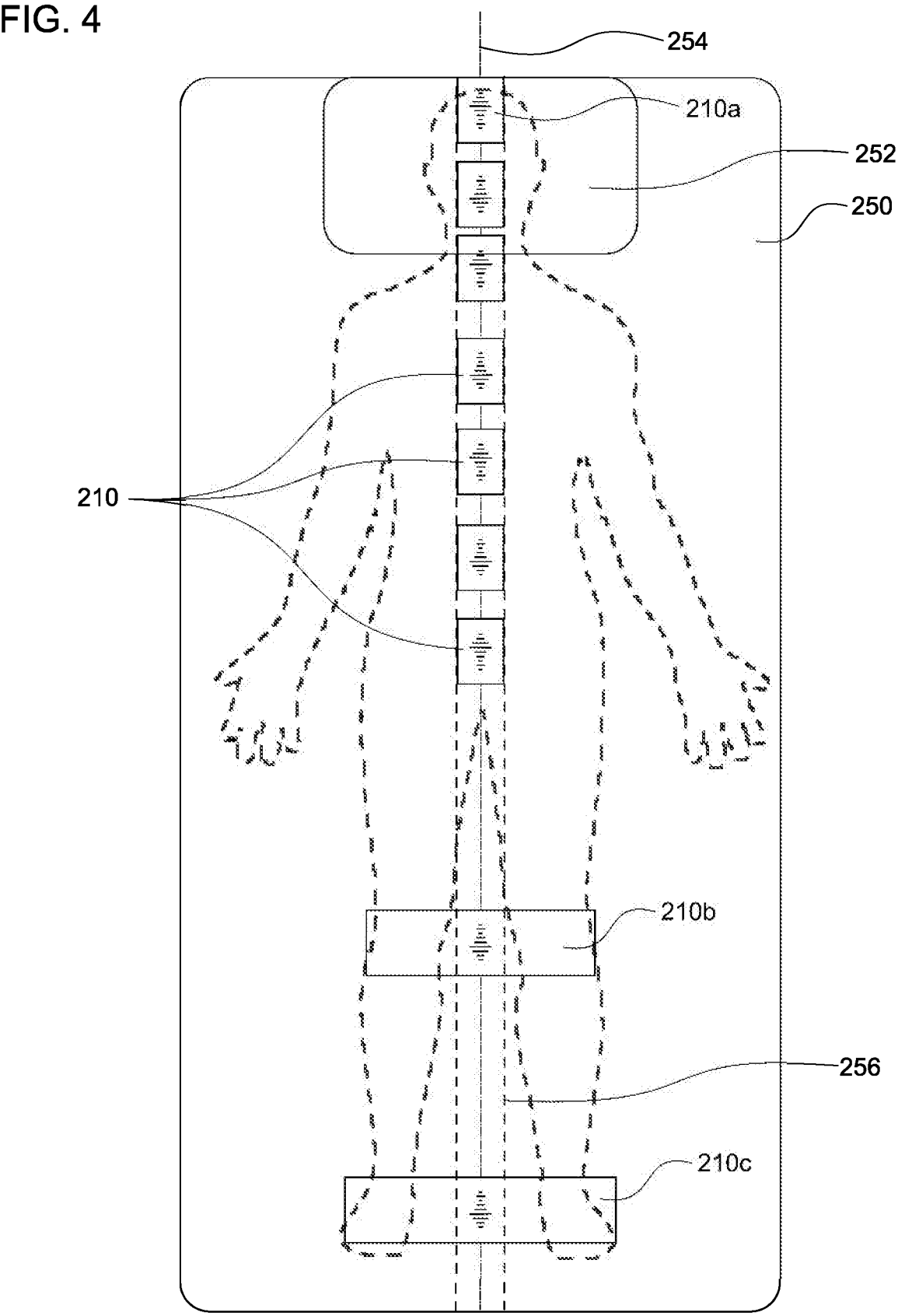
FIG. 4 is an illustration of the relaxation substrate of FIG. 3, according to various embodiments.

FIG. 3 is a detailed illustration of the system of FIG. 1, according to an embodiment. FIG. 4 is an illustration of the relaxation substrate 250 of, e.g., FIG. 3, according to various embodiments.

According to an embodiment, referring to FIGS. 3 and 4, the system 100 further includes a relaxation substrate 250 disposed and oriented to receive the user. In an embodiment, each vibration module 210 of the plurality of vibration modules 200 is disposed along a longitudinal axis 254 of the relaxation substrate 250. At least one of the vibration modules 210 of the plurality of vibration modules 200 may be disposed along a track 256 of the relaxation substrate 250. In one embodiment, a position of at least one of the vibration modules 210 is adjustable along the track 256 of the relaxation substrate 250. Additionally and/or alternatively, the track 256 supplies electrical power to at least one of the vibration modules 210, and/or the vibration modules 210 may be electrically connected one to the next. In one embodiment, the relaxation substrate 250 includes a mat, a pad, or a mattress, such that the user may lie down, e.g., in a supine or side position. In an alternative embodiment, the relaxation substrate 250 includes a chair 8200, a seat, or a sofa, and engages the user when the user is in a seated position. (See discussion of FIG. 8, below.)

According to an embodiment, referring to FIGS. 3 and 4, the system 100 further includes a pillow member 252. At least a head-position vibration module 210a of the plurality of vibration modules 200 may be disposed in the pillow member 252. In an embodiment, the pillow member 252 is attached to the relaxation substrate 250.

According to an embodiment, referring again to FIGS. 3 and 4, each vibration module 210 of the plurality of vibration modules 200 may be embedded within the relaxation substrate 250. Each vibration module 210 of the plurality of vibration modules 200 may further include a base, the base having an attachment element (not shown) configured for removably attaching the vibration module 210 to the relaxation substrate 250. In an embodiment, the base may include a height adjustment element (e.g., mechanical, pneumatic, hydraulic).

According to an embodiment, referring to FIGS. 1-4, at least one vibration module 210 of the plurality of vibration modules 200 is configured for attachment to the respective predetermined body site of the user. The attachment configuration for the at least one vibration module 210 may include an adhesive, a hook and loop attachment, and/or a strap. In an embodiment, the plurality of vibration modules 200 includes nine (9) vibration modules 210 disposed, for a human user, at a head position (see vibration modules 210a), a neck position (corresponding to 210a), an upper back position, an upper-mid back position, a lower-mid back position, a lumbar position, a gluteal position (see positions of modules placed between 210a and 210b), a knee position (see 210b), and a heel/foot position (see 210c). A position of at least one vibration module 210 of the plurality of vibration modules 200 may be adjustable by the user along an axis of adjustment (e.g., along the user's spine). In one embodiment, the vibration module 210c at the heel/foot position may be adjustably disposed behind the user's heel. In another embodiment, the vibration module 210c at the heel/foot position may be oriented against the sole of at least one of the user's feet (not shown). Applicant contemplates that vibration modules 210 placed in correspondence with knees and feet may be configured to affect both knees or both feet simultaneously. Such configuration may include a larger vibration element or multiple vibration elements distributed across a width corresponding to the width of a user's knees and/or feet, or separate vibration modules for each side. According to an embodiment, the vibration modules 210b, 210c may be adjustable from side to side to accommodate different sized users, as well as an configuration for position adjustment backward and forward.

According to an embodiment, at least one vibration module 210 of the plurality of vibration modules 200 includes a power source (not shown). In an embodiment, the power source is a replaceable battery.

According to an embodiment, at least one vibration module 210 of the plurality of vibration modules 200 includes a power source 218. In an embodiment, the power source 218 is a replaceable battery.

According to an embodiment, at least one vibration module 210 of the plurality of vibration modules 200 is configured for wireless communication with the controller 400. Each vibration module 210 of the plurality of vibration modules 200 may be separately controllable by the controller 400. For example, each vibration module 210 may include communication circuitry configurable to have a unique address with respect to other vibration modules 210 such that communication between the controller 400 and a respective vibration module 210 may include an address of the vibration module and/or of the controller.

Figure 6:
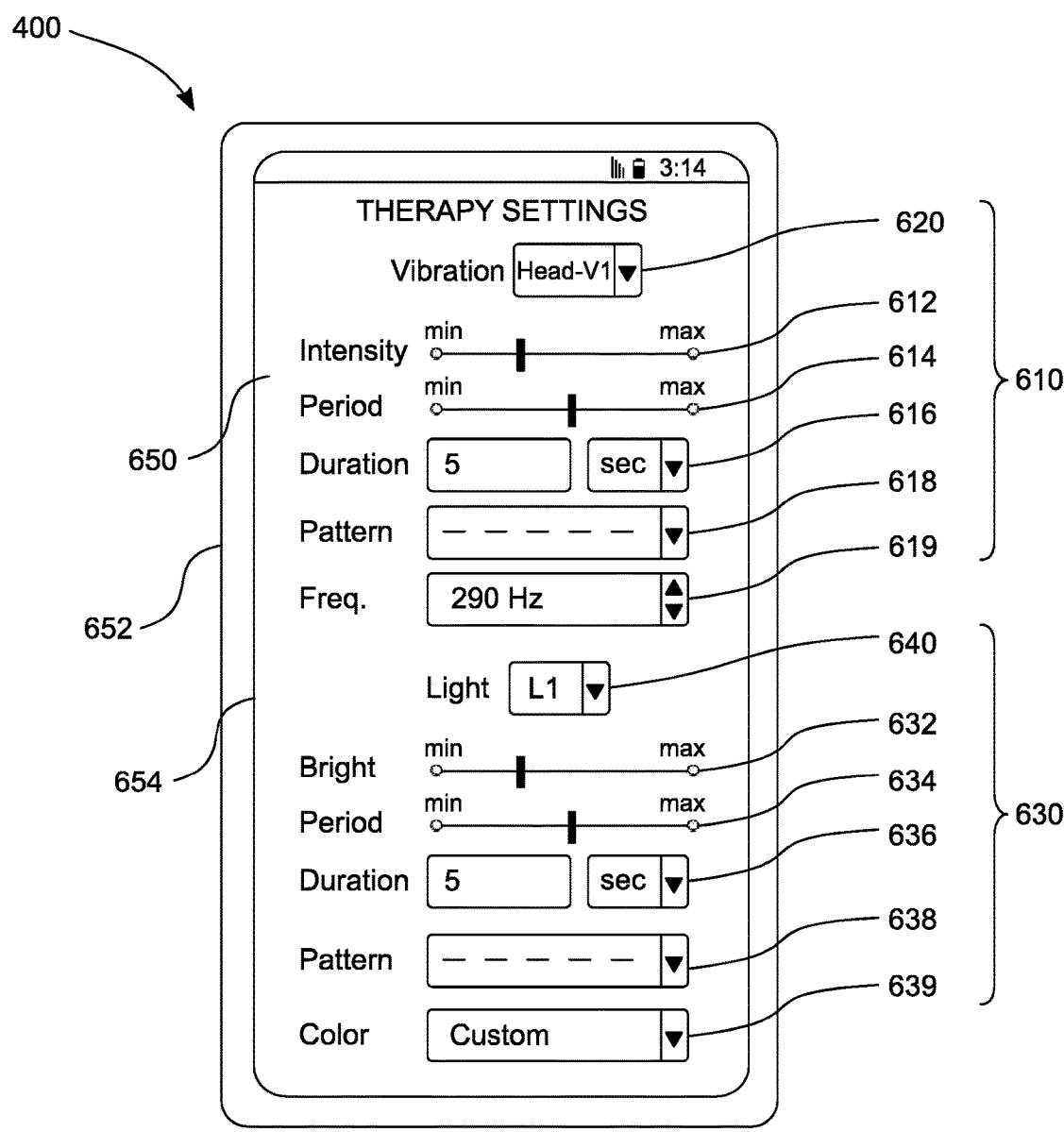
FIG. 6 is an illustration of a graphical user interface (GUI), according to an embodiment.

According to an embodiment, referring to FIGS. 3 and 6, the light-providing member 300 may include a plurality of light-providing modules 310 respectively disposed at the light positions. The plurality of light-providing modules 310 may include incandescent or fluorescent bulbs, LEDs, or the like, for example. The light-providing member 300 may be a light bar or other monolithic element incorporating the light-providing modules 310 for connection to a wall or ceiling. According to an embodiment, one or more of the light-providing modules 310 may be disposed separate from the others. For example, in FIG. 3, light-providing module 310a may be disposed on a wall, headboard, or the like 312 at a position nearer where the user's head would lie during use. In another embodiment, at least one of the light-producing modules (e.g., 310c) may be physically larger than the other light-producing modules 310.

The placement and distribution of light producing areas may correspond to the placement and distribution of the vibration modules 210. For example a light-providing area 310a may be disposed to correspond, directly or proportionally, with placement of the vibration module 210a, disposition of a light providing area 310b may correspond with position of a vibration module 210b, a light-providing area 310c may correspond with a vibration module 210c, etc. In some implementations, the light-providing areas may be considered, in the user's thoughts, as corresponding with major bodies of the solar system. For example, the light producing area corresponding to the user's head (or foot) may correspond to the sun, followed by light providing areas corresponding to Mercury, Venus, Earth, Mars, Jupiter, Saturn, Neptune, and Uranus.

In an embodiment, the light-providing member 300 may include one or more a securing devices (not shown). Such securing device may include adhesive, screw holes, or a bar connecting all lights, etc., for example. In an embodiment, each light-providing module 310 includes a respective securing device. In one embodiment, the securing device includes a light attachment bar 350 to which at least one of the light-providing modules 310 is secured in an adjustable position along the light attachment bar 350. The attachment bar 350 may be secured by screws, a receptacle, a track, etc. The light attachment bar 350 may supply electrical communication for the at least one light-providing module 310, the electrical communication including at least one of electrical power and a control signal from the controller 400.

Figure 2B:
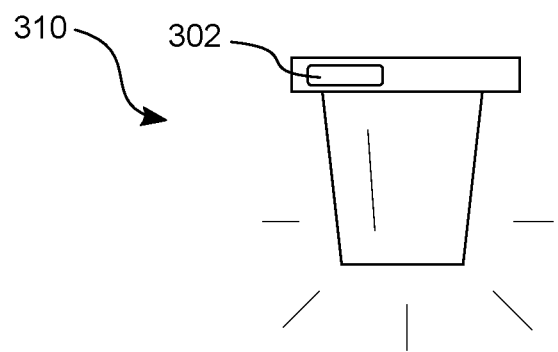
FIG. 2B is an illustration of a light-providing module 310 including a respective power source.

According to an embodiment, referring to FIGS. 1, 3 and 6, the light-providing member 300 may include a power source. In one embodiment, each light-providing module 310 includes a respective power source 302. For example, the light-providing module 310 may be plugged into an electrical outlet. In another embodiment, as shown in FIG. 2B, the power source 302 may be a battery.

According to an embodiment, the plurality of light positions corresponds in number with the number of vibration modules 210 of the plurality of vibration modules 200. According to another embodiment, the light-providing member 300 is configured to cause light to appear at respective light positions of the plurality of light positions in a predetermined, repeatable sequence. The configuration to cause light to appear at the respective light positions includes causing the light to appear with predetermined characteristics including at least one of color, intensity, saturation, duration, and periodicity for each light position.

Figure 5:
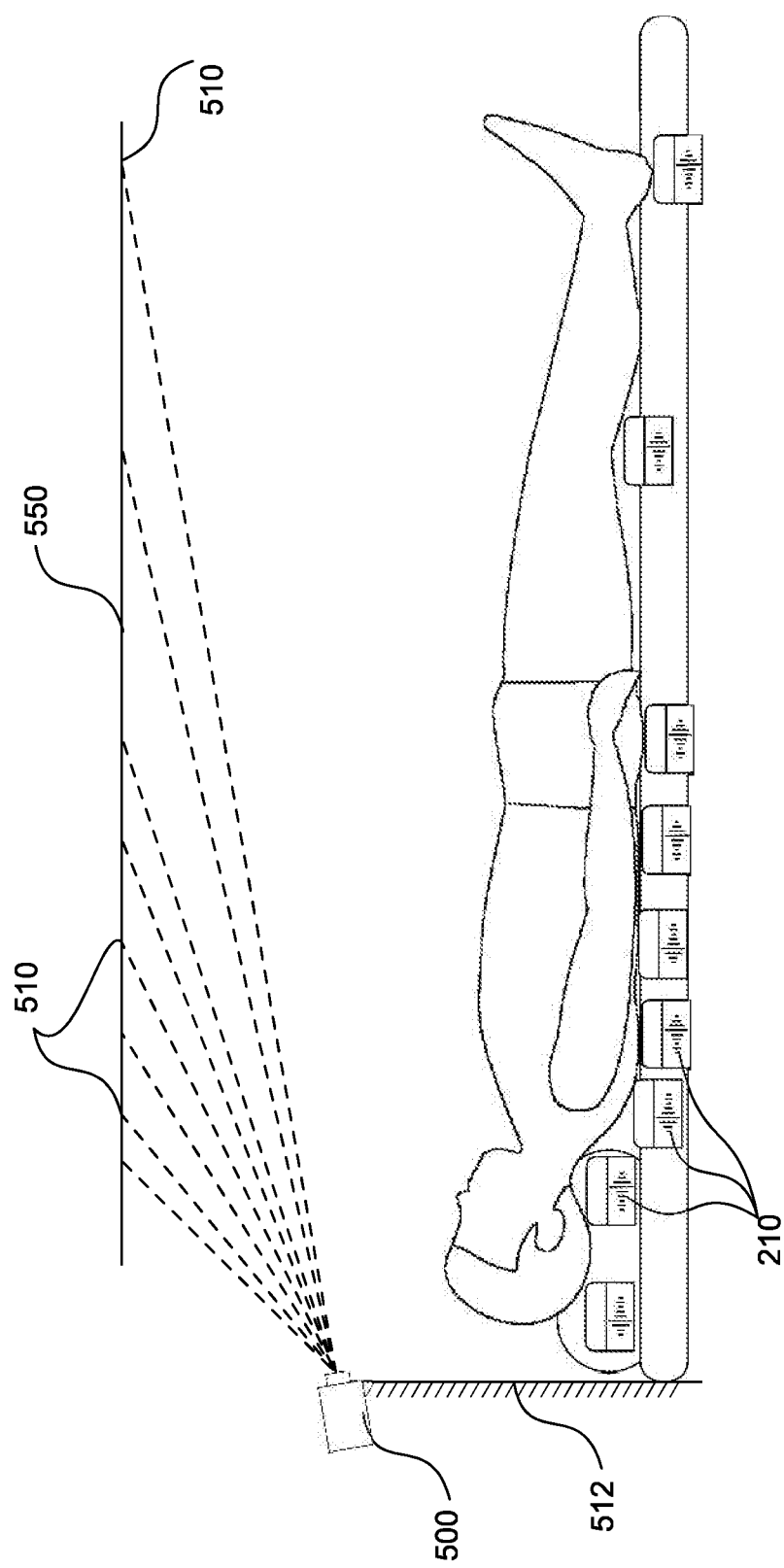
FIG. 5 is an illustration of the system of FIG. 1, including an alternative light-providing member 500, according to various embodiments.

FIG. 5 is an illustration of the system of FIG. 1, including an alternative light-providing member 500, according to various embodiments. The light-providing member 500 may direct light to each of a plurality of light positions 510 from a first location 512. The light providing member 500 may include a projector or a laser (see FIG. 5). The plurality of light positions 510 may include areas of a ceiling 550 or a wall (see FIG. 8), or may include a positions on a display screen (not shown). The first location 512 may include a shelf, a desk, a table, or a wall, for example, in different implementations. The light-providing member 500 may include an attachment feature for attachment to the first location 512 (e.g., a wall area above the user's head when lying down or sitting). In another embodiment, the light-providing member 500 may be embedded within a wall. In another embodiment, the light-providing member 500 may include a light-direction adjustment feature, such as a height and/or angle adjustment. Additionally and/or alternatively, the light-providing member 500 includes a laser.

FIG. 6 is an illustration of a graphical user interface (GUI) 650, according to an embodiment, as an example of a controller 400. Those having ordinary skill in the art will recognize that elements of the GUI in FIG. 6 may be applicable to a dedicated or built-in controller 400 as well as a portable or app-based controller 400. References are thus made primarily to an app-based controller 400, recognizing that many or all of the features may be employed in a dedicated device.

According to an embodiment, referring again to FIGS. 1, 3 and 6, the controller 400 further includes a control interface (e.g., GUI 650) configured to receive an input from the user for changing a status of the relaxation system 100 (e.g., on, off, standby, etc.). The control interface may further include a display screen (e.g., 654) configured to display features relevant to the system 100. The features relevant to the system 100 may include at least one of a status of the system 100 and an input for adjusting control characteristics. In an embodiment, the display screen 654 of the control interface includes a touch screen. In another embodiment, the display screen 654 is part of a personal electronic device 652 configured to perform control of the apparatus.

The controller 400 (such as personal electronic device 652) may include a non-volatile computer readable medium (not shown) having stored thereon instructions for the control of the system 100. The instructions for the control of the system 100 may constitute at least part of an application stored on a mobile device. The instructions for the control of the system 100 may be downloadable. The controller 400 may include or be configured to use communication circuitry configured to receive and transmit data, including the instructions, measurements, user-entered data, sensor data, and the like via WiFi, Bluetooth, cellular network, etc. The controller 400 (such as personal electronic device 652) may include a processor, peripheral inputs and outputs, and/or one or more communication circuits (e.g., radios), and may be attachable wirelessly (e.g., via Bluetooth, NFC, WiFi, or the like) or via wire (e.g., USB) to a dedicated control interface of the system 100. In an embodiment, the controller 400 may include a physical button, a physical switch, a physical slider, and/or a physical turning knob (see, e.g., 410 in FIG. 3).

According to an embodiment, referring to FIG. 6, the GUI 650 may be the user interface of an application used on a personal electronic device such as a cell phone, tablet, personal computer, or the like.

According to an embodiment, referring to FIGS. 1, 3 and 6, the controller 400 may include vibration controllers 610 respectively configured to control, in at least one vibration module 210 of the plurality of vibration modules 200, an intensity of vibration 612, a period of vibration 614, a duration of vibration 616, a pattern of vibration 618, and/or a frequency of vibration 619. Settings from the vibration controllers 610 may, in an embodiment, be applied to all of the vibration modules 210 or to a particular subset of the vibration modules 210, e.g., via a vibration module selector 620.

According to an embodiment, the controller 400 may include light controllers 630 respectively configured to control, in the light-providing member 300, 500, a brightness 632, a period of light production 634, a duration 636, a pattern 638, and/or a color 639 for each light position or light-providing module 310. Another control or screen may show, and/or permit selection of, a sequence of control for the lights or light-providing modules 310, the duration between illumination of each light-providing area, and the like. Settings from the light controllers 630 may, in an embodiment, be applied to all of the light providing areas or positions 310 or to a particular subset of the light providing areas 310, e.g., via a light-providing module selector 640.

According to an embodiment, referring to FIGS. 1 and 3, the controller 400 may include a wireless communication radio (not shown) for communication with at least one of the vibration modules 210 or at least a portion of the light-providing member 300 or with both the at least one vibration module 210 and the at least a portion of the light-providing member 300.

Figure 7:
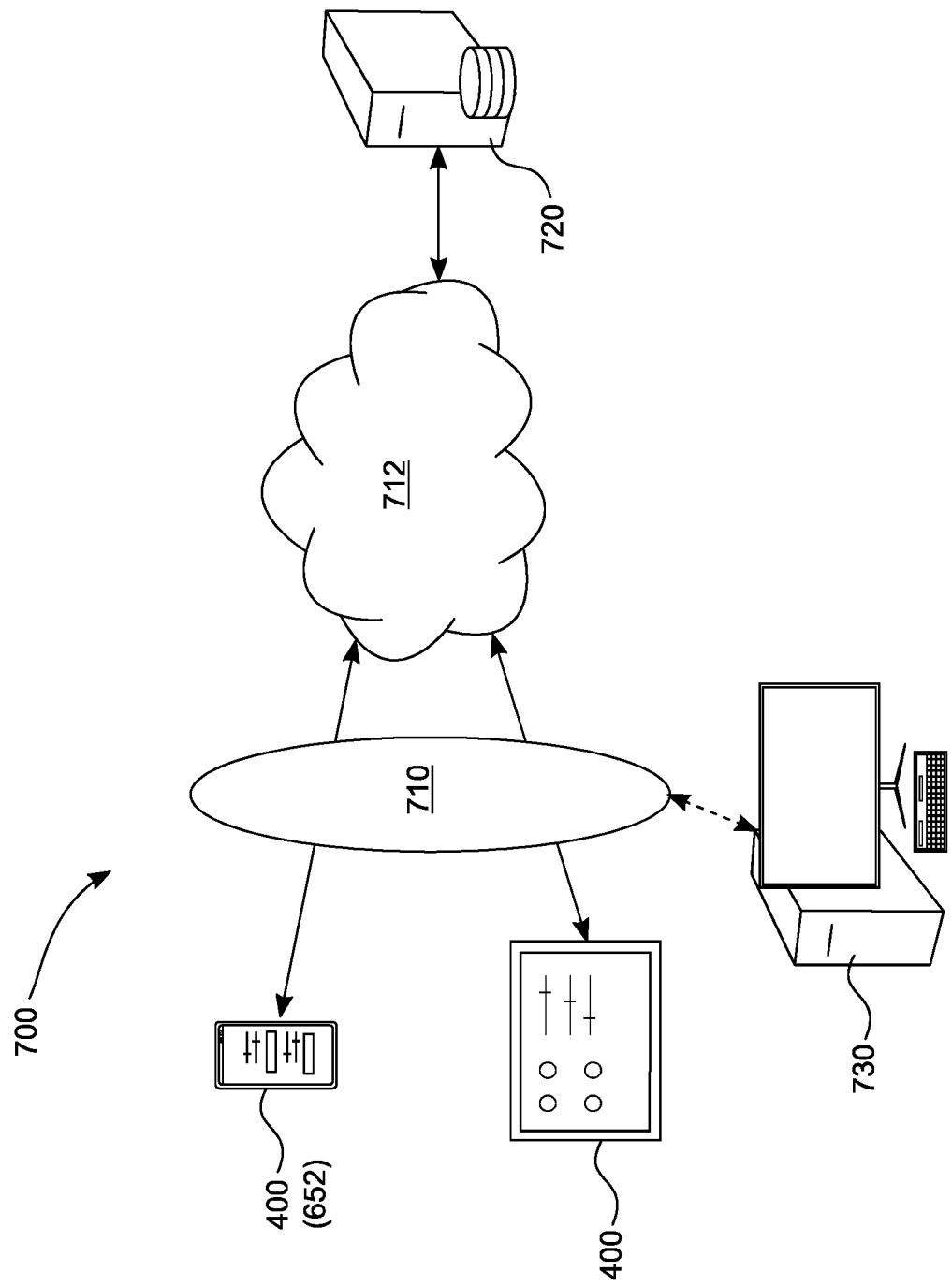
FIG. 7 is a diagram of a network connectivity for the system of FIG. 1, according to an embodiment.

FIG. 7 is a diagram of a network connectivity 700 for the controller 400 of, e.g., FIGS. 1, 3, and 6, according to an embodiment.

According to an embodiment, referring to FIG. 7, the controller 400 includes network connection circuitry (not shown). The network connection circuitry may be configured to provide data communication between the controller 400 and at least one of a local area network 710 and the Internet 712. For example, data communication between the controller 400 (e.g., 652) and at least one of a local area network 710 and the Internet 712 may be via WiFi, cellular, or wired communication. In another embodiment, the controller 400 is further configured to provide data to a computer server 720 or local computer 730 (e.g., via the local area network 710 or via the Internet 712).

Referring momentarily to FIG. 3, the system 100 may include one or more sensors 450 (see FIG. 3) configured to measure a characteristic of the user, and the controller 400 may be configured to collect data from the one or more sensors 450 and send it to the computer server 720 or local computer 730. Additionally, the controller 400 may receive data from the computer server 720, such as software/firmware updates, user information such as a goal progress, user encouragement, etc.

The one or more sensors 450 may be configured to detect and/or measure one or more characteristics of the user. The characteristics of the user may include one or more of the user's heart rate, blood pressure, sleep pattern, brain wave record, usage data, user data, sweat chemistry, dryness, temperature or the like. One or more sensors may be implemented to detect and report maintenance information, software information, software debugging, remote control, etc. of the system 100. Sensor(s) 450 may be disposed, without limitation, in body-attached devices such as a wrist-watch-type device, ear-lobe connection, adhesive probes, sensors embedded in a substrate (e.g., substrate 250, or may be configured to measure ambient conditions, including, for example, room temperature, humidity, sound level, etc. In an embodiment, the controller 400 is configured to at least temporarily store the data from the one or more sensors 450. In another embodiment, the controller 400 is configured to analyze the data received from the one or more sensors 450. The analyzed data may be used, for example, to show improvement, to keep record of use, to include a reward system for consistency, etc. In some embodiments, the sensor data may be accumulated collectively from many users and used for marketing, advertising, population-based health statistics, or the like.

Figure 8:
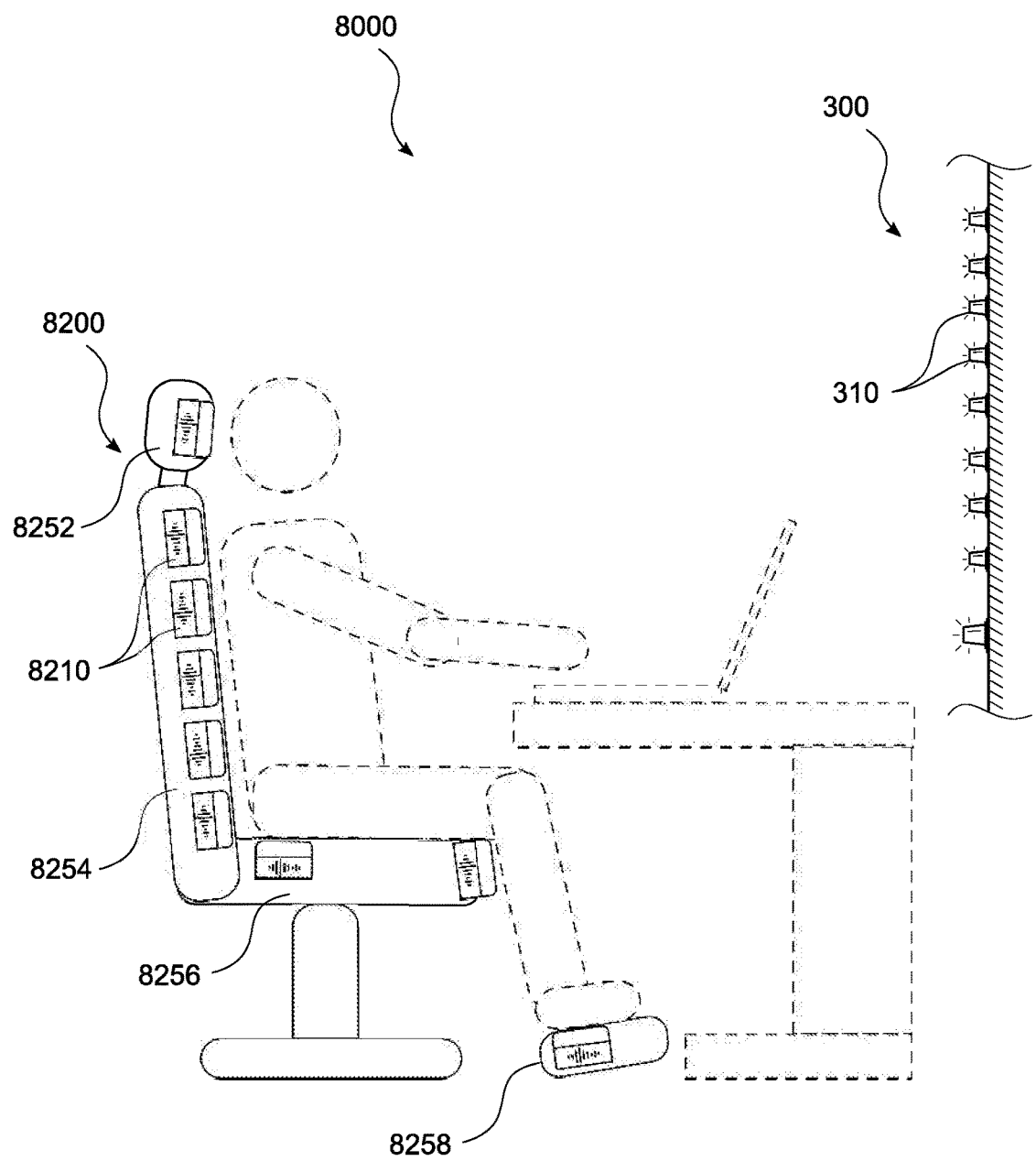
FIG. 8 is a detailed illustration of the system of FIG. 1, according to an alternative embodiment.

FIG. 8 is a detailed illustration of an alternative implementation in which a relaxation system 8000 including a relaxation substrate that engages a user when the user is in a seated position, according to an embodiment. For example, FIG. 8 illustrates a chair 8200 that includes a plurality of vibration modules 8210 distributed along a headrest 8252, seat back 8254, seat 8256, and footrest 8258. It is contemplated that the chair may include a reclining mechanism, such that it may be used for a dentist chair, a medical waiting room chair, a vehicle seat, or the like. In such implementation, the light-providing member 300 may be implemented on or along a wall, or on a computer screen or the like, where a user may comfortably see each light-providing module 310.

Figure 9:
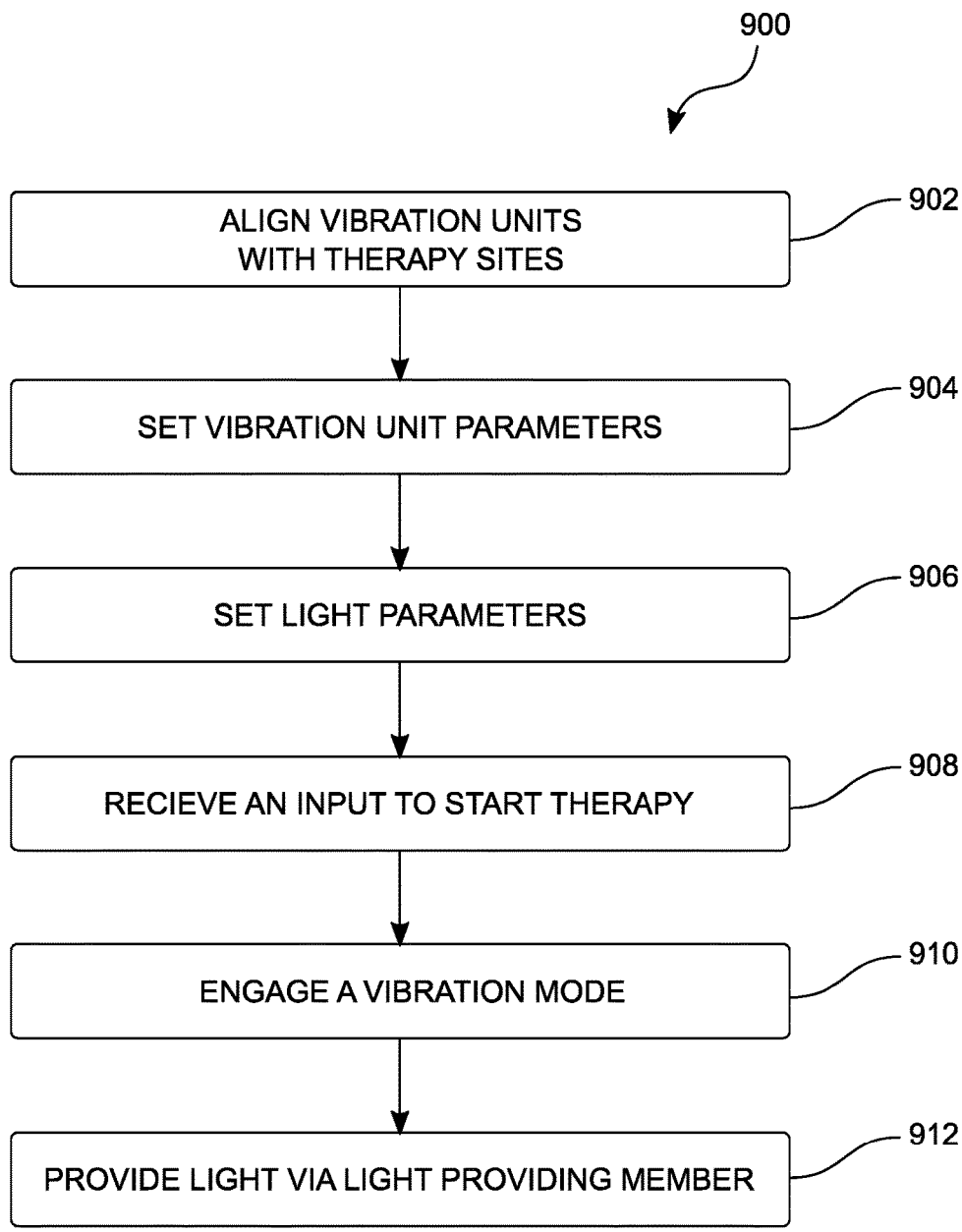
FIG. 9 is a flow chart showing a method for inducing relaxation, according to an embodiment.

FIG. 9 is a flow chart showing a method 900 for inducing relaxation, according to an embodiment. The method 900 for inducing relaxation includes, in step 902, aligning a plurality of vibration units (e.g., 210 of FIGS. 1-5) respectively arranged to correspond to predetermined therapy sites of a user's body. Step 904 includes positioning a plurality of light-providing areas within view of a user relaxation position. Step 906 includes setting, via a controller (e.g., the controller 400), one or more vibration parameters of at least one vibration unit of the plurality of vibration units. Step 908 includes setting, via the controller, at least one light parameter of a light-providing member. Step 910 includes receiving an input, via the controller, to begin a therapy session. Step 912 includes selectively engaging a vibration mode of each vibration unit of the plurality of vibration units consistent with said setting of the at least one vibration parameter. Step 914 includes selectively providing light to the light-providing areas via the light-providing member consistent with the at least one light parameter.

According to an embodiment, in step 902, the aligning of the plurality of vibration units includes aligning the vibration units in a line between a user first position and a user second position. The first position may be a user head position and the second position may be a user foot position.

According to an embodiment, the plurality of light-providing areas, in step 904, corresponds in number with a number of vibration modules in the plurality of vibration modules.

According to an embodiment, the setting of the at least one light parameter of a light-providing member, in step 908, includes setting color, intensity, saturation, duration, and/or periodicity of light provided to one or more of the light-providing areas.

According to an embodiment, the setting of the at least one vibration parameter of at least one vibration unit of the plurality of vibration units, in step 906, includes setting an intensity of vibration, a period of vibration, a duration of vibration, a pattern of vibration, and/or a frequency of vibration.

In some embodiments, default light parameters and/or default vibration parameters may be set at a predetermined time, such as during manufacture, and the controller may default to such default parameters. In other embodiments, a user may save parameters for re-use at a later time, or may save different sets of parameters for use in different settings or for different purposes (e.g., relaxation, energization, stress reduction, pain reduction, or the like). In another embodiment, multiple users may save respective settings for light and vibration according to personal preference, and the setting may be recalled for later use at the controller.

According to an embodiment, the positioning of the plurality of light-providing areas, in step 904, corresponds to positioning of the plurality of vibration units.

According to an embodiment, the selectively engaging of the vibration mode, in step 912, and the selectively providing light, in step 914, are performed in synchronization, such that each light-providing area of the plurality of light-providing areas illuminates substantially simultaneously with engagement of a corresponding vibration unit.

According to an embodiment, in step 904, the plurality of light-providing areas includes nine (9) light-sourcing elements. In one embodiment, each of the light-sourcing elements is an LED.

According to an embodiment, each light-providing area of the plurality of light-providing areas is a target area for a light-projecting device. The light-providing device may be a laser. Each target area may include a reflective material.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:
1. A system, comprising:
a plurality of vibration modules, each vibration module of the plurality of vibration modules configured to provide a vibration to a respective predetermined back-side body site of a user;
a light-providing member configured to provide light at a plurality of light positions viewable opposite the plurality of vibration modules; and
a controller operably connected to the plurality of vibration modules and the light-providing member, the controller configured to control at least one of a light characteristic of the light provided by the light-providing member and a vibration characteristic of the vibration provided by said each vibration module, wherein the light-providing member is configured to cause light to appear at respective light positions of the plurality of light positions in a predetermined, repeatable sequence with predetermined characteristics including at least one of color, intensity, saturation, duration, and periodicity for each light position.

2. The system according to claim 1, wherein each vibration module of the plurality of vibration modules includes a vibration member.

3. The system according to claim 2, wherein
each vibration member includes a linear resonant actuator, and
the controller includes a current generator configured to energize the linear resonant actuator with an oscillating current to cause linear oscillation of a mass of the linear resonant actuator.

4. The system according to claim 2, wherein each vibration member includes an eccentric rotating mass vibration motor, and
the controller includes a current generator configured to energize the eccentric rotating mass vibration motor.

5. The system according to claim 2, wherein each vibration module further includes a cushion member.

6. The system according to claim 5, wherein the cushion member is replaceable and is selected from a plurality of cushion members respectively having at least one of a different thickness and a different firmness.

7. The system according to claim 6, wherein the vibration member is disposed within the replaceable cushion member.

8. The system according to claim 1, further comprising a relaxation substrate disposed and oriented to receive the user.

9. The system according to claim 8, wherein the plurality of vibration modules is disposed along a longitudinal axis of the relaxation substrate.

10. The system according to claim 9, wherein at least one of the vibration modules of the plurality of vibration modules is disposed along a track of the relaxation substrate.

11. The system according to claim 10, wherein a position of at least one of the vibration modules is adjustable along the track of the relaxation substrate.

12. The system according to claim 10, wherein the track supplies electrical power to at least one of the vibration modules.

13. The system according to claim 8, wherein the relaxation substrate includes a mat, a pad, or a mattress.

14. The system according to claim 8, wherein the relaxation substrate includes a chair, a seat, or a sofa, and engages the user when the user is in a seated position.

15. The system according to claim 8, further comprising a pillow member, wherein at least a head-position vibration module of the plurality of vibration modules is disposed in the pillow member.

16. The system according to claim 15, wherein the pillow member is attached to the relaxation substrate.

17. The system according to claim 8, wherein each of the plurality of vibration modules is embedded within the relaxation substrate.

18. The system according to claim 8, wherein each vibration module of the plurality of vibration modules further includes a base, the base having an attachment element configured for removably attaching the vibration module to the relaxation substrate.

19. The system according to claim 18, wherein the base includes a height adjustment element.

20. The system according to claim 1, wherein at least one vibration module of the plurality of vibration modules is configured for attachment to the respective predetermined body site of the user.

21. The system according to claim 20, wherein the attachment configuration for the at least one vibration module includes at least one of: an adhesive, a hook and loop attachment, and a strap.

22. The system according to claim 1, wherein the plurality of vibration modules includes nine (9) vibration modules disposed, for a human user, at a head position, a neck position, an upper back position, an upper-mid back position, a lower-mid back position, a lumbar position, a gluteal position, a knee position, and a heel/foot position.

23. The system according to claim 22, wherein a position of at least one vibration module of the plurality of vibration modules is adjustable by the user along an axis of adjustment.

24. The system according to claim 22, wherein the vibration module at the heel/foot position is adjustably disposed behind the user's heel.

25. The system according to claim 22, wherein the vibration module at the heel/foot position is configured to be oriented against the sole of at least one of the user's feet.

26. The system according to claim 1, wherein at least one vibration module of the plurality of vibration modules includes a power source.

27. The system according to claim 26, wherein the power source is a replaceable battery.

28. The system according to claim 1, wherein each vibration module of the plurality of vibration modules is connected by at least one wire directly or indirectly to the controller.

29. The system according to claim 1, wherein at least one vibration module of the plurality of vibration modules is configured for wireless communication with the controller.

30. The system according to claim 29, wherein each vibration module of the plurality of vibration modules is separately controllable by the controller.

31. The system according to claim 1, wherein the light-providing member includes a plurality of light-providing modules respectively disposed at the light positions.

32. The system according to claim 31, wherein the light-providing member includes a securing device.

33. The system according to claim 32, wherein the securing device includes a light attachment bar to which at least one of the light-providing modules is secured in an adjustable position along the light attachment bar.

34. The system according to claim 31, wherein the controller is configured to control, in at least one of the light-providing modules of the light-providing member, at least one of: a brightness, a color, a sequence, a duration, and a period of light production.

35. The system according to claim 33, wherein the light attachment bar supplies electrical communication for the at least one light-providing module, the electrical communication including at least one of electrical power and a control signal from the controller.

36. The system according to claim 1, wherein the light-providing member includes a power source.

37. The system according to claim 36, wherein each light-providing module includes a respective power source.

38. The system according to claim 37, wherein the power source is a battery.

39. The system according to claim 1, wherein the plurality of light positions corresponds in number with the number of vibration modules of the plurality of vibration modules.

40. The system according to claim 1, wherein the light-providing member directs light to each of the plurality of light positions from a first location.

41. The system according to claim 40, wherein the light-providing member includes a laser.

42. The system according to claim 1, wherein the controller includes vibration controllers respectively configured to control, in at least one vibration module of the plurality of vibration modules, at least one of: an intensity of vibration, a period of vibration, a duration of vibration, a pattern of vibration, and a frequency of vibration.

43. The system according to claim 1, wherein the controller includes light controllers respectively configured to control, in the light-providing member, at least one of: a brightness, a period of light production, a duration, a pattern, a color, and a sequence.

44. The system according to claim 1, wherein the controller includes a wireless communication radio for communication with at least one of the vibration modules or at least a portion of the light-providing member or with both the at least one vibration module and the at least a portion of the light-providing member.

45. The system according to claim 1, wherein the controller includes a control interface comprising a display screen configured to display features relevant to the apparatus.

46. The system according to claim 45, wherein the features relevant to the apparatus include at least one of a status of the apparatus and an input for controlling the control characteristics.

47. The system according to claim 45, wherein the display screen of the control interface includes a touch screen.

48. The system according to claim 45, wherein the display screen is part of a personal electronic device configured to perform control of the apparatus.

49. The system according to claim 48, wherein the personal electronic device comprises a non-volatile computer readable medium having stored there on instructions for the control of the apparatus.

50. The system according to claim 1, wherein the controller includes a control interface comprising at least one of: a physical button, a physical switch, a physical slider, and a physical turning knob.

51. The system according to claim 1, wherein the controller includes network connection circuitry.

52. The system according to claim 51, wherein the network connection circuitry is configured to provide data communication between the controller and at least one of a local area network and the Internet.

53. The system according to claim 51, wherein the controller is further configured to provide data to a computer server.

54. The system according to claim 53, further comprising one or more sensors configured to measure a characteristic of the user, wherein the controller is configured to send data from the one or more sensors to the computer server.

55. The system according to claim 1, further comprising one or more sensors configured to measure a characteristic of the user.

56. The system according to claim 55, wherein the controller is configured to at least temporarily store data from the one or more sensors.

57. The system according to claim 56, wherein the controller is configured to analyze data from the one or more sensors.

58. The system according to claim 1, wherein the controller further comprises a control interface configured to receive an input from the user for changing a status of the apparatus.

* * * * *